US010918828B2

(12) United States Patent
Egley et al.

(10) Patent No.: US 10,918,828 B2
(45) Date of Patent: Feb. 16, 2021

(54) KINK AND COMPRESSION TOLERANT MEDICAL TUBING

(71) Applicant: Fresenius Medical Care Holdings, Inc., Waltham, MA (US)

(72) Inventors: Bert D. Egley, Walnut Creek, CA (US); Jon Moss, Antioch, CA (US); Daniel Schmidt, Petaluma, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 39 days.

(21) Appl. No.: 15/978,414

(22) Filed: May 14, 2018

(65) Prior Publication Data

US 2019/0344045 A1 Nov. 14, 2019

(51) Int. Cl.
*A61M 25/00* (2006.01)
*A61M 1/28* (2006.01)

(52) U.S. Cl.
CPC ........ *A61M 25/0043* (2013.01); *A61M 1/285* (2013.01); *A61M 25/003* (2013.01); *A61M 2025/0031* (2013.01); *A61M 2025/0059* (2013.01); *A61M 2205/70* (2013.01)

(58) Field of Classification Search
CPC .............. A61M 25/0043; A61M 1/285; A61M 25/003; A61M 2025/0031; A61M 2025/0059; A61M 2205/70; A61M 1/14; A61M 1/16; A61M 1/1089; A61M 39/287; A61M 39/283
See application file for complete search history.

(56) References Cited

U.S. PATENT DOCUMENTS

| 1,596,754 A | 8/1926 | Moschelle |
| 1,928,992 A | 10/1933 | Clark et al. |
| 3,720,235 A * | 3/1973 | Schrock ................ F16L 11/121 138/137 |
| 3,957,054 A | 5/1976 | McFarlane |
| 4,131,399 A | 12/1978 | Calvet |

(Continued)

FOREIGN PATENT DOCUMENTS

| EP | 428616 | 5/1991 |
| EP | 1917987 | 5/2008 |

(Continued)

OTHER PUBLICATIONS

International Search Report and Written Opinion in Application No. PCT/US2019/027840, dated Sep. 5, 15 pages.

(Continued)

*Primary Examiner* — Lauren P Farrar
(74) *Attorney, Agent, or Firm* — Fish & Richardson P.C.

(57) ABSTRACT

Medical fluid tubing described herein is configured to be advantageously tolerant of kinking and/or crushing. That is, the tubing is configured such that even if the tubing is kinked or fully compressed at least some portion of the lumen defined by the tubing will remain open, and some fluid will continue to flow through the tubing. Such kink and compression tolerant medical tubing can be advantageously used in association with medical fluid pumping systems (e.g., peritoneal dialysis systems and the like). In some examples, the tubing described herein is used in conjunction with, or as a part of, a medical fluid cassette that interfaces with such medical fluid pumping systems.

7 Claims, 13 Drawing Sheets

(56) References Cited

U.S. PATENT DOCUMENTS

| | | | |
|---|---|---|---|
| 4,257,422 A | 3/1981 | Duncan | |
| 4,398,910 A * | 8/1983 | Blake | A61M 25/0071 604/266 |
| 4,579,555 A | 4/1986 | Russo | |
| 4,681,570 A | 7/1987 | Dalton | |
| 4,811,928 A * | 3/1989 | Iwatschenko | A61M 39/28 251/4 |
| 4,867,485 A | 9/1989 | Seckel | |
| 4,923,223 A | 5/1990 | Seckel | |
| 5,215,450 A | 6/1993 | Tamari | |
| 5,682,925 A | 11/1997 | Seckel | |
| 7,918,247 B2 | 4/2011 | Coleman | |
| 8,443,845 B2 | 5/2013 | Tomlin et al. | |
| 8,684,967 B2 | 4/2014 | Engel et al. | |
| 9,067,040 B2 | 2/2015 | Byrnes et al. | |
| 2005/0230292 A1 * | 10/2005 | Beden | A61M 1/1037 210/85 |
| 2011/0146829 A1 | 6/2011 | Coleman | |
| 2013/0192598 A1 | 8/2013 | Tomlin et al. | |
| 2014/0276421 A1 | 9/2014 | Plahey et al. | |
| 2014/0358118 A1 * | 12/2014 | Hayakawa | A61B 5/150633 604/506 |
| 2016/0030708 A1 * | 2/2016 | Casiello | A61M 25/0043 604/218 |
| 2017/0021130 A1 * | 1/2017 | Dye | A61M 25/04 |

FOREIGN PATENT DOCUMENTS

| | | |
|---|---|---|
| EP | 2032194 | 3/2009 |
| WO | WO 2009/065552 | 5/2009 |

OTHER PUBLICATIONS

PCT International Preliminary Report on Patentability in International Appln. No. PCT/US2019/027840, dated Nov. 26, 2020, 11 pages.

* cited by examiner

KINK AND COMPRESSION TOLERANT MEDICAL TUBING

TECHNICAL FIELD

This disclosure relates to tubing for medical fluid pumping systems and related devices and methods.

BACKGROUND

Dialysis is a treatment used to support a patient with insufficient renal function. The two principal dialysis methods are hemodialysis and peritoneal dialysis.

During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), a patient's peritoneal cavity is periodically infused with dialysis solution or dialysate. The membranous lining of the patient's peritoneum acts as a natural semi-permeable membrane that allows diffusion and osmosis exchanges to take place between the solution and the blood stream. These exchanges across the patient's peritoneum, like the continuous exchange across the dialyzer in HD, result in the removal of waste products, including solutes like urea and creatinine, from the blood, and regulate the levels of other substances, such as sodium and water, in the blood.

Automated PD machines called PD cyclers are designed to control the entire PD process so that it can be performed at home, usually overnight without clinical staff in attendance. This process is termed continuous cycler-assisted PD (CCPD). Many PD machines are designed to automatically infuse, dwell, and drain dialysate to and from the patient's peritoneal cavity. The treatment typically lasts for several hours, often beginning with an initial drain procedure to empty the peritoneal cavity of used or spent dialysate. The sequence then proceeds through the succession of fill, dwell, and drain phases that follow one after the other. Each phase is called a cycle.

SUMMARY

In one aspect, this disclosure is directed to a medical fluid cassette. The medical fluid cassette includes a base member, a flexible membrane attached to the base member such that the membrane and the base member cooperate to define one or more fluid flow paths within the medical fluid cassette, and a tube extending from the medical fluid cassette. The tube is in fluid communication with the one or more fluid flow paths. The tube defines a central longitudinal axis and including internal ribs extending inwardly from an inner wall of the tube toward the central longitudinal axis.

Such a medical fluid cassette may optionally include one or more of the following features. The internal ribs of the tube may have triangular cross-sectional shapes. The tube may include three of the internal ribs. The internal ribs may have heights in a range of 40 percent to 46 percent of an inner radius of the tube. Apices of the triangular cross-sectional shapes may point toward the central longitudinal axis at a geometric center of a cross-section of the tube. The medical fluid cassette may be a peritoneal dialysis fluid cassette. The tube may be a patient line attached to the peritoneal dialysis fluid cassette. The tube may have a durometer of shore 70.

In another aspect, this disclosure is directed to a medical tubing system. The medical tubing system includes a medical tube defining a central longitudinal axis and including internal ribs extending inwardly from an inner wall of the tube toward the central longitudinal axis, and a tube closure device. The tube closure device includes a sleeve defining an opening that slidingly receives the tube, a set of jaws coupled to the sleeve and radially deflectable in relation to the sleeve, and a clamp collar positioned around at least portions of set of jaws and longitudinally movable in relation to the set of jaws.

Such a medical tubing system may optionally include one or more of the following features. The clamp collar may be longitudinally movable in relation to the set of jaws between: (i) a first position in which the set of jaws are in an open configuration and (ii) a second position in which the clamp collar deflects the set of jaws radially inward in comparison to the open configuration. Each jaw of the set of jaws may include a ramp surface that slidingly mates against a corresponding annular ramp surface of the clamp collar. The clamp collar may be threadedly mated to the sleeve. The clamp collar may include an internal thread that threadedly mates with an external thread of the sleeve. Each jaw of the set of jaws may be radially alignable with a respective internal rib of the tube while the tube closure device is positioned on the tube. The tube may include three internal ribs, and the set of jaws may include three jaws. The tube may define longitudinal grooves extending along an outer surface of the tube that are radially aligned with the internal ribs.

In another aspect, this disclosure is directed to a kink and compression tolerant medical tube. The tube defines a central longitudinal axis and includes internal ribs extending inwardly from an inner wall of the tube toward the central longitudinal axis. The tube has a durometer in a range of shore 65 to shore 75.

Such a kink and compression tolerant medical tube may optionally include one or more of the following features. The internal ribs may have triangular cross-sectional shapes. Apices of the triangular cross-sectional shapes may point toward the central longitudinal axis at a geometric center of a cross-section of the tube. The tube may include three of the internal ribs. The internal ribs may have heights in a range of 40 percent to 46 percent of an inner radius of the tube. The internal ribs may spiral around the central longitudinal axis.

Implementations can include one or more of the following advantages.

In certain implementations, the tubing and systems described herein can enhance the efficacy of patient medical treatments because the tubing resists occlusion due to kinking and/or compression. That is, even though the tubing may become kinked or compressed, the tubing will continue to have an open lumen to allow for fluid flow. Accordingly, medical treatments can take place with fewer treatment interruptions, fewer alarms, and faster cycle times.

In some implementations, patient safety is improved because even while the tubing is kinked or crushed, some flow through the tubing will continue and the medical treatment will proceed. Moreover, the tubing described herein can be kink and compression tolerant while maintaining a desirable level of flexibility or compliance. Such flexible kink and compression tolerant tubing mitigates the potential for inducing stress to the patient's tissue from lateral forces on a catheter that may otherwise occur from stiffer types of kink and compression tolerant tubing.

In certain implementations, the patient's experience and comfort is improved using the kink and compression tolerant tubing and systems described herein. Even though the tubing is kink and compression tolerant, it is also compliant in bending, resulting in enhanced patient comfort in comparison to stiffer tubing. Additionally, treatment system alarms due to tubing occlusions may be reduced using the kink and compression tolerant tubing and systems described herein. As such, the patient may experience more relaxation during treatment, and get better sleep in some cases.

In certain implementations, when blood is being transported using the kink and compression tolerant tubing described herein, the tubing will tend to reduce the potential for inducement of hemolysis. The reduced potential for hemolysis results because, even though the tubing may become kinked or compressed, the tubing will continue to have an open lumen to allow for the blood to flow.

Other aspects, features, and advantages will be apparent from the description and drawings, and from the claims.

DETAILED DESCRIPTION

This disclosure relates generally to tubing that can be used in association with medical fluid pumping systems (e.g., PD systems, hemodialysis systems, hemofiltration systems, hemodiafiltration systems, etc.) and other medical devices/systems. In some examples, the tubing described herein is used in conjunction with, or as a part of, a medical fluid cassette that interfaces with such medical fluid pumping systems. In some cases the tubing described herein may be connected to a patient via a catheter, and may be used to convey fluids such as, but not limited to, dialysis solution (or "dialysate"), spent dialysate (or "effluent"), blood, saline, medications, water, ionized water, air, oxygen, other gasses, and so on. Such fluids may be conveyed to the patient from the medical system, or from the patient to the medical system or elsewhere.

As described further below, the tubing described herein is designed and configured to be advantageously tolerant of kinking and/or crushing. That is, even if the tubing is kinked or compressed (or "crushed"), at least some portion of the lumen defined by the tubing will remain open and some fluid will continue to flow through the tubing.

The kink and compression tolerant tubing is described below using the example context of a PD system. It should be understood, however, that a PD system is merely one of the contexts in which the kink and compression tolerant tubing described herein can be beneficially used.

Figure 1:
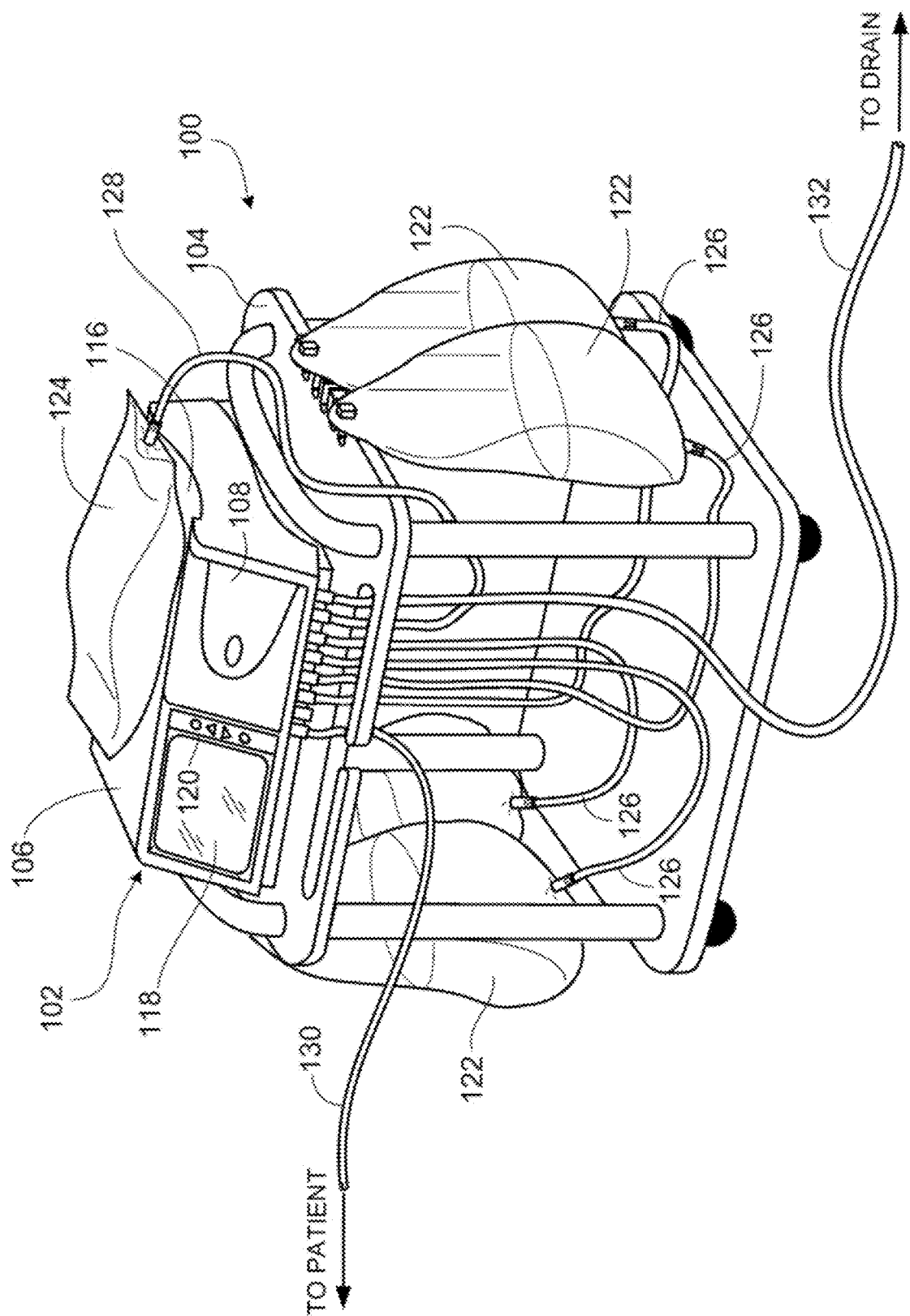
FIG. 1 is a perspective view of a peritoneal dialysis ("PD") system that includes a PD cycler positioned atop a portable cart.
Figure 2:
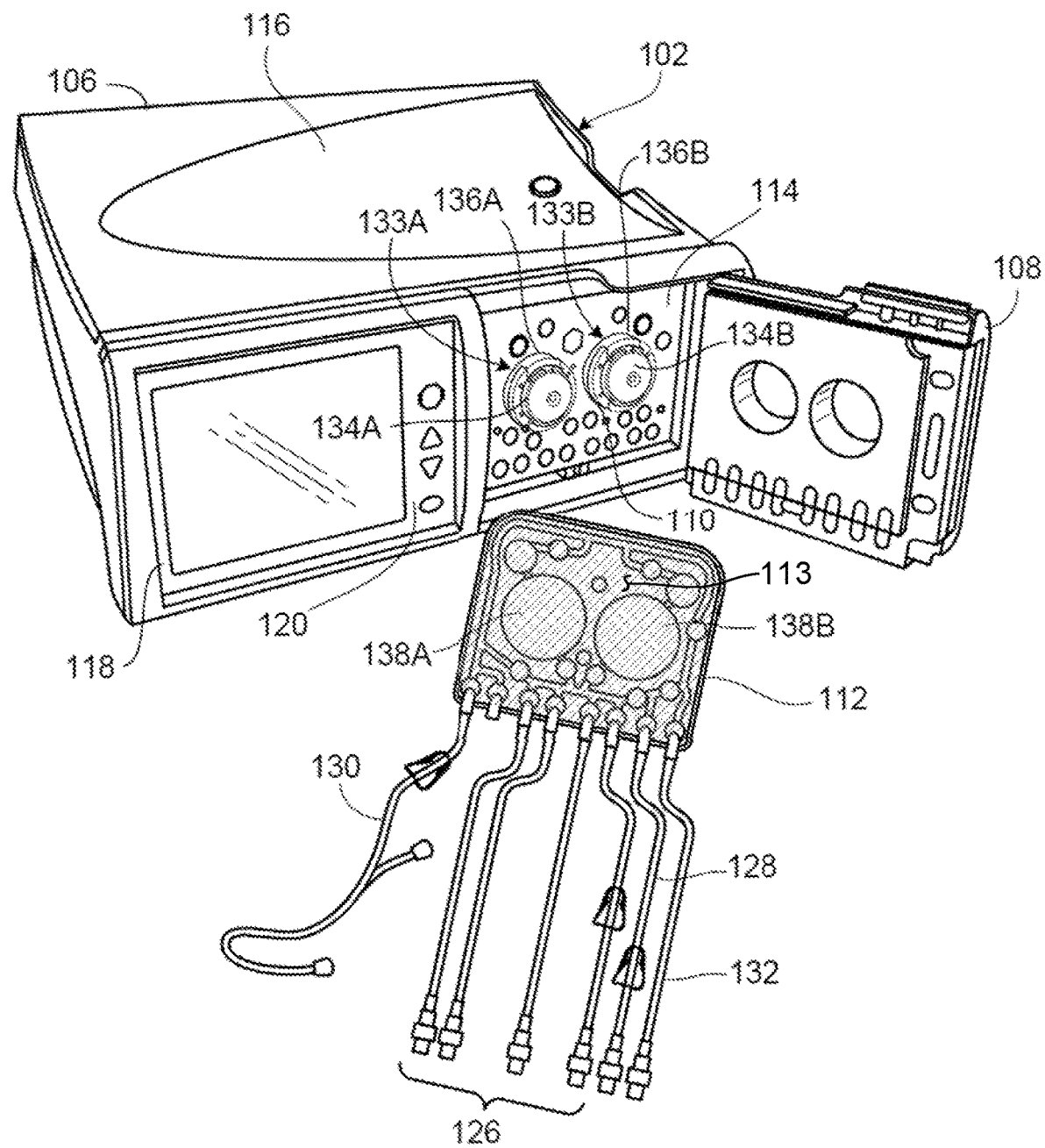
FIG. 2 is a perspective view of the PD cycler and a PD cassette of the PD system of FIG. 1. A door of the PD cycler is in the open position to show the inner surfaces of the PD cycler that interface with the PD cassette during use.

Referring to FIGS. 1 and 2, an example PD system 100 includes a PD cycler (also referred to as a PD machine) 102 seated on a cart 104. The PD cycler 102 includes a housing 106, a door 108, and a cassette interface 110 that abuts a disposable PD cassette 112 when the cassette 112 is disposed within a cassette compartment 114 formed between the cassette interface 110 and the closed door 108. A heater tray 116 is positioned on top of the housing 106. The heater tray 116 is sized and shaped to accommodate a bag of dialysis solution (e.g., a five liter bag of dialysis solution). The PD cycler 102 also includes a touch screen 118 and additional control buttons 120 that can be operated by a user (e.g., a patient) to allow, for example, set-up, initiation, and/or termination of a PD treatment.

Dialysis solution bags 122 are suspended from fingers on the sides of the cart 104, and a heater bag 124 is positioned on the heater tray 116. The dialysis solution bags 122 and the heater bag 124 are connected to the cassette 112 via dialysis solution bag lines 126 and a heater bag line 128, respectively. The dialysis solution bag lines 126 can be used to pass dialysis solution from dialysis solution bags 122 to the cassette 112 during use, and the heater bag line 128 can be used to pass dialysis solution back and forth between the cassette 112 and the heater bag 124 during use. In addition, a patient line 130 and a drain line 132 are connected to the cassette 112. The patient line 130 can be connected to a patient's abdomen via a catheter, and can be used to pass dialysis solution back and forth between the cassette 112 and the patient during use. The drain line 132 can be connected to a drain or drain receptacle and can be used to pass dialysis solution from the cassette 112 to the drain or drain receptacle during use. The spent dialysate is also referred to as effluent herein.

The cassette 112 generally includes a rigid plastic molded base member and a flexible membrane 113 attached to the base. The base and the membrane 113 of the cassette 112 cooperate to define various dialysis solution channels and dialysis solution chambers integrally within the cassette 112. The cassette 112 is configured to align with various valve actuators, sensors and other components of the PD cycler 102 when the cassette 112 is coupled with the PD cycler 102. The cassette 112 can be a single-use disposable element used for a PD treatment.

FIG. 2 shows a more detailed view of the cassette interface 110 and the door 108 of the PD cycler 102. As shown, the PD cycler 102 includes pistons 133A, 133B with piston heads 134A, 134B that can be axially moved within piston access ports 136A, 136B formed in the cassette interface 110. The pistons 133A, 133B include shafts that are connected to motors that can be operated to move the piston heads 134A, 134B axially inward and outward within the piston access ports 136A, 136B. When the cassette 112 is positioned within the cassette compartment 114 of the PD cycler 102 with the door 108 closed, the piston heads 134A, 134B of the PD cycler 102 align with pump chambers 138A, 138B of the cassette 112 such that the piston heads 134A, 134B can be mechanically connected to fastening members of the cassette 112 overlying the pump chambers 138A, 138B. As a result of this arrangement, movement of the piston heads 134A, 134B toward the cassette 112 during treatment can decrease the volume of the pump chambers 138A, 138B, and force dialysis solution out of the pump chambers 138A, 138B, while retraction of the piston heads 134A, 134B away from the cassette 112 can increase the volume of the pump chambers 138A, 138B and cause dialysis solution to be drawn into the pump chambers 138A, 138B.

Still referring to FIGS. 1 and 2, during PD treatment, the patient line 130 extending from the cassette 112 is connected to a patient's abdomen via a catheter, and the drain line 132 is connected to a drain or drain receptacle. The PD treatment typically begins by emptying the patient of spent dialysis solution that remains in the patient's abdomen from the previous treatment. To do this, the pump of the PD cycler 102 is activated to cause the pistons 133A, 133B to reciprocate to cause the spent dialysis solution to be drawn from the patient into the patient line 130, and then to the fluid pump chambers 138A, 138B of the cassette 112. The spent dialysis solution is then pumped from the fluid pump chambers 138A, 138B to the drain via the drain line 132.

After draining the spent dialysis solution from the patient, heated dialysis solution is transferred from the heater bag 124, through the cassette 112, and to the patient via the patient line 130. To do this, the motor or motors of the PD cycler 102 is/are activated to cause the pistons 133A, 133B to reciprocate and certain inflatable members 142 of the PD cycler 102 are inflated to cause the warmed dialysis solution to be drawn into the fluid pump chambers 138A, 138B of the cassette 112 from the heater bag 124 via the heater bag line 128. The warmed dialysis solution is then pumped from the fluid pump chambers 138A, 138B to the patient via the patient line 130.

Once the dialysis solution has been pumped from the heater bag 124 to the patient, the dialysis solution is allowed to dwell within the patient for a period of time. During this dwell period, toxins cross the peritoneum of the patient into the dialysis solution from the patient's blood. As the dialysis solution dwells within the patient, the PD cycler 102 prepares fresh dialysate for delivery to the patient in a subsequent cycle. In particular, the PD cycler 102 pumps fresh dialysis solution from one of the four full dialysis solution bags 122 into the heater bag 124 for heating. To do this, the pump of the PD cycler 102 is activated to cause the pistons 133A, 133B to reciprocate and certain inflatable members 142 of the PD cycler 102 are inflated to cause the dialysis solution to be drawn into the fluid pump chambers 138A, 138B of the cassette 112 from the selected dialysis solution bag 122 via its associated line 126. The dialysis solution is then pumped from the fluid pump chambers 138A, 138B to the heater bag 124 via the heater bag line 128.

After the dialysis solution has dwelled within the patient for the desired period of time, the spent dialysis solution is pumped from the patient through the patient line 130, and then to the drain via drain line 132. The heated dialysis solution is then pumped from the heater bag 124 and through the patient line 130 to the patient where it dwells for a desired period of time. These steps are repeated with the dialysis solution from two of the three remaining dialysis solution bags 122. The dialysis solution from the last dialysis solution bag 122 is typically delivered to the patient via the patient line 130 and left in the patient until the subsequent PD treatment.

PD treatments (e.g., as described above) usually occur at night while the patient is sleeping. A PD treatment typically involves several fills and drains of many liters of dialysate fluid, and may occur over the entire night. In some circumstances, the patient line 130 (connected to the patient) may inadvertently become obstructed to fluid flow because of unintentional kinking or pinching (crushing) of the patient line 130 tubing. For example, the patient may simply roll over while sleeping, causing the patient line 130 to become partially or fully kinked or crushed. In that case, the PD treatment can be partially or fully inhibited, disrupted, and/or discontinued.

Most PD systems have one or more pressure sensors to monitor the fluid pressure in the patient line 130. Those pressure sensors can detect when the patient line 130 has become obstructed because of being partially or fully kinked or crushed. In such a case, the PD system (e.g., the PD cycler 102) may pause the treatment and deliver an alert/alarm in attempt to wake the patient. An awakened patient will then need to check for kinks and/or compression of the patient line 130, resolve the problem, and then resume treatment. Unfortunately for the patient, this scenario may repeat itself many times during a night.

One potential way to mitigate the problem of the patient line 130 becoming obstructed because of kinking or crushing is to make the patient line 130 stiff so that it is very resistant to bending and compression. In some cases, metal wires are embedded in the wall of tubing for such purposes. However, if the tubing used for the patient line 130 is made very stiff (resistant to bending and compression), then the tubing tends to be very uncomfortable for the patient to use. For example, when the patient rolls over during sleep, the stiff tube used for the patient line 130 will likely cause substantial stress and pain to the patient via lateral forces exerted by the catheter to the patient.

Accordingly, making the patient line 130 flexible while also tolerant to kinking and crushing will provide a more effective PD treatment (e.g., with less interruptions), and a better patient experience (e.g., with fewer alarms and fewer required interventions). That is, tubing that is flexible and that will allow for flow through the tubing even while kinked or crushed will provide many benefits when used as the patient line 130 for the PD system 100 (and for other medical uses).

Figure 3:
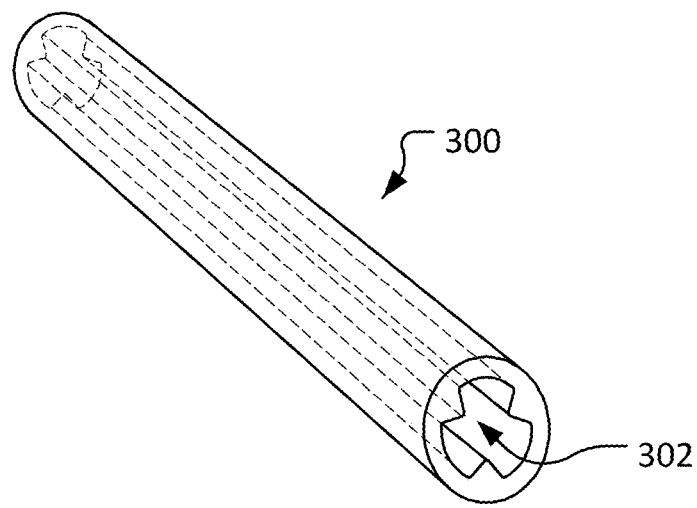
FIG. 3 is a perspective view of an example tube that is kink and compression tolerant.
Figure 4:
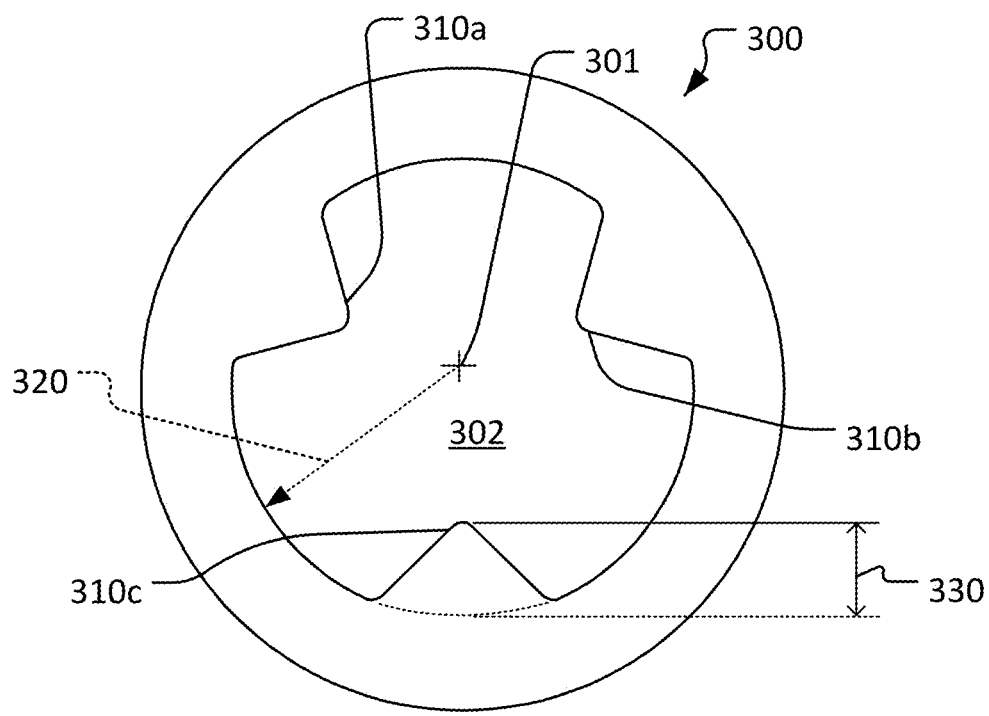
FIG. 4 is a cross-sectional view of the tube of FIG. 3.

Referring to FIGS. 3 and 4, a portion of an example kink and compression tolerant medical tubing 300 (or simply "tubing 300") is illustrated. FIG. 4 shows a cross-sectional shape of the tubing 300. As described further below, the kink and compression tolerant medical tubing 300 can be advantageously used as the patient line 130 (FIGS. 1 and 2), for example.

The tubing 300 can be made from any suitable polymeric material, such as polyvinyl chloride (PVC). In some embodiments, the PVC material has a durometer of shore 70. In some embodiments, the durometer of the PVC material is in a range of shore 65 to shore 75, or shore 60 to shore 80, or shore 55 to shore 85. The tubing 300 is preferably sufficiently flexible and compliant so that movements of the patient that result in bending of the tubing 300 do not induce stress at the location where the tubing 300 is percutaneously attached to the patient (e.g., via a catheter). In the depicted embodiment, there is no reinforcing wire/material within the wall of the tubing 300.

The tubing 300 is scalable to any suitable size. In one example embodiment the outer diameter of the tubing 300 is 6.0 mm and the inner diameter of the tubing 300 is 4.0 mm (hence, the inner radius 320 is 2.0 mm). The tubing 300 can be made to have any suitable length.

The tubing 300 defines a single lumen 302 through which fluid can flow. The lumen 302 is the open space within the tubing 300. The tubing 300 includes three internal ribs 310a, 310b, and 310c (or collectively "ribs 310a-c"). In the depicted embodiment, the ribs 310a-c are triangular projections that extend inward from the inner wall of the tubing. Each of the triangular ribs 310a-c includes an apex, and the ribs 310a-c are arranged such that the apices are pointed towards a geometric center 301 of the tubing 300. The triangular ribs 310a-c are arranged at about 120 degrees relative to each other around the 360 degree inner circumference of the tubing 300. A central longitudinal axis of the tubing 300 extends along the geometric center 301.

In the depicted embodiment, the ribs 310a-c and the wall of the tubing 300 are contiguous and made of the same material (e.g., by extrusion). The lumen 302 is the open space within the tubing 300 (and does not include the area of the ribs 310a-c).

Each of the ribs 310a-c extends inward from the inner wall of the tubing 300 for a distance that is referred to as the rib height 330. The rib height 330 is less than the inner radius 320. As described further below, the inventors have discovered that when the rib height 330 is 43% of the inner radius 320, the size of the lumen 302 is maximized while the tubing 300 is fully compressed.

Figure 5:
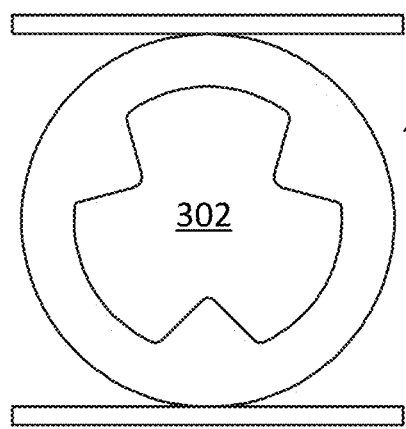
FIG. 5 shows a cross-sectional view of the tube of FIG. 3 while compressed by a first amount.
Figure 6:
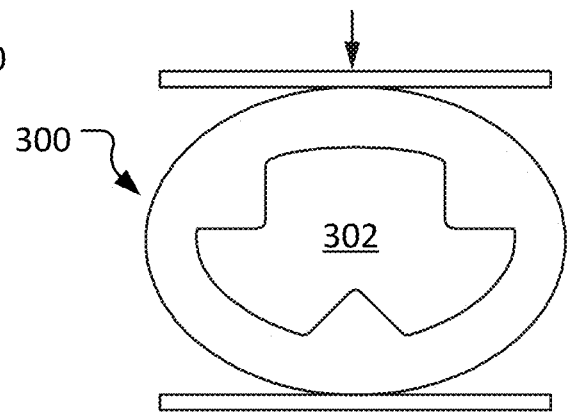
FIG. 6 shows a cross-sectional view of the tube of FIG. 3 while compressed by a second amount that is greater than the first amount.
Figure 7:
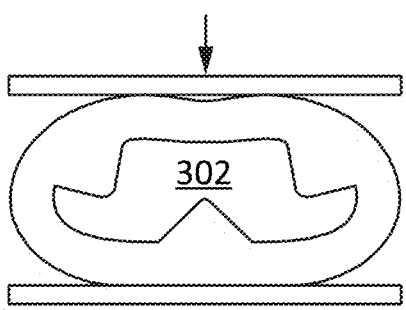
FIG. 7 shows a cross-sectional view of the tube of FIG. 3 while compressed by a third amount that is greater than the second amount.
Figure 8:
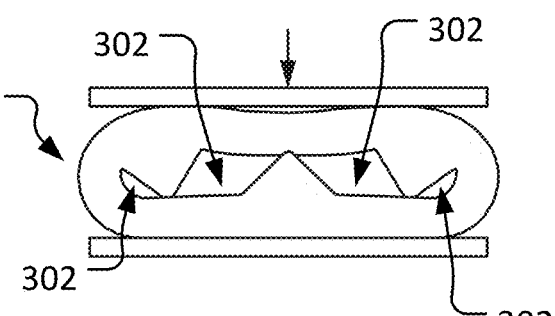
FIG. 8 shows a cross-sectional view of the tube of FIG. 3 while compressed by a fourth amount that is greater than the third amount.

FIGS. 5-8 depicts the tubing 300 in four differing states of lateral compression. This type of compression to the tubing 300 may be induced, for example, by kinking (bending), by pure lateral compression (crushing), or by a combination of both. In FIG. 5, the tubing 300 is not compressed or deformed. In FIG. 8, the tubing 300 is considered to be fully compressed (e.g., the apex of each of the three ribs 310a-c is in contact with the inner wall of the tubing 300). FIGS. 6 and 7 depict successive degrees of compression between FIGS. 5 and 8.

It can be seen that the cross-section of the lumen 302 is shaped differently in each of the depicted differing states of compression. Actually, the lumen 302 is divided up into multiple separated portions while the tubing 300 is in the fully compressed state (shown in FIG. 8). In this particular example, the lumen 302 is divided up into four separated open area portions while the tubing 300 is in the fully compressed state.

The tubing 300 is kink and compression tolerant because, as FIG. 8 illustrates, even though the tubing 300 is fully compressed there is/are still open area(s) (the lumen 302) that allows fluid to flow through the tubing 300. As stated above, the inventors have discovered that when the rib height 330 is 43% of the inner radius 320, the open area of the lumen 302 is maximized while the tubing 300 is fully compressed.

Figure 9:
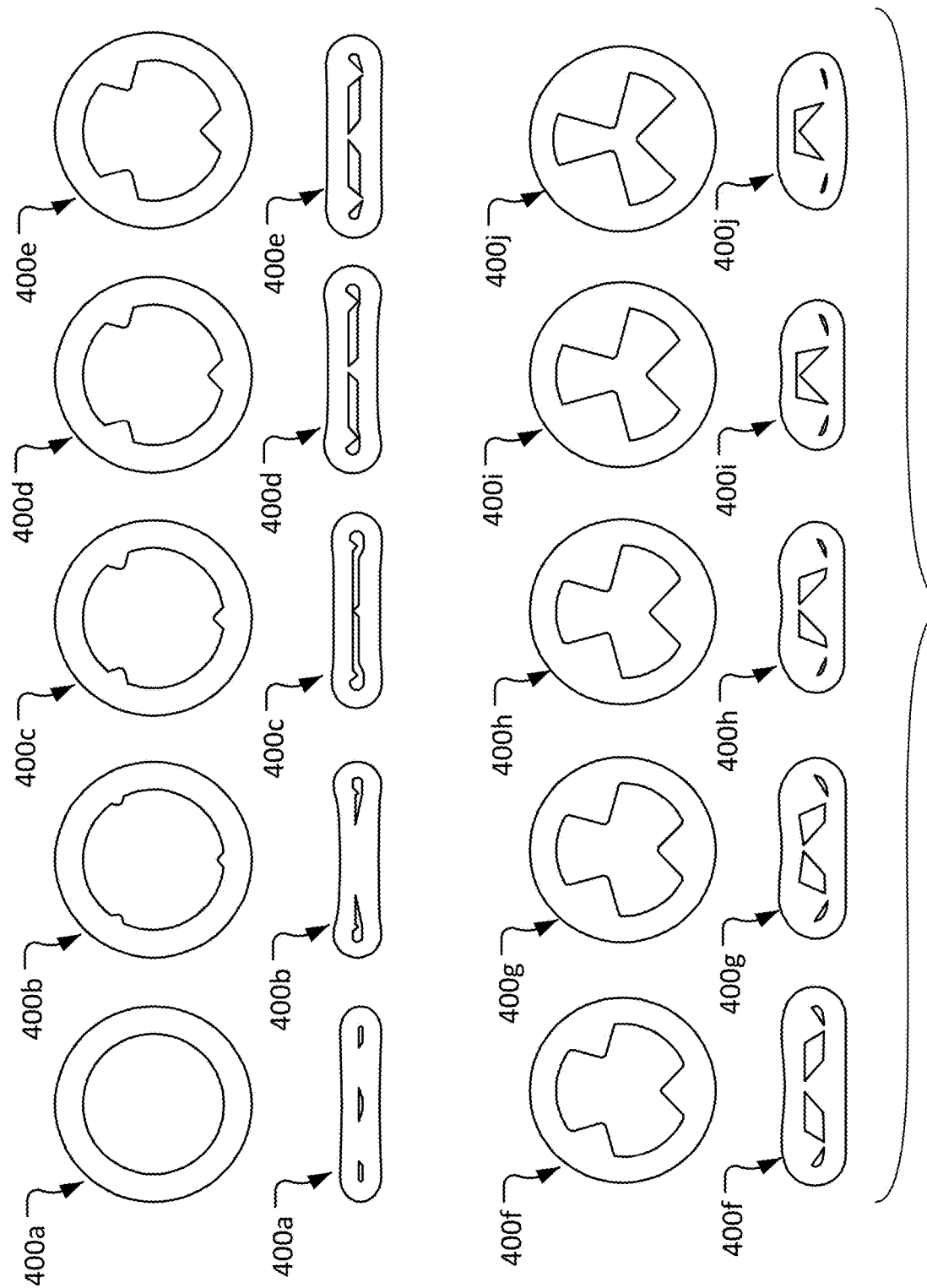
FIG. 9 shows cross-sectional views of various tubes that have differing rib heights. Each type of tube is shown in an uncompressed configuration and a greatly compressed configuration.

Referring to FIG. 9, cross-sections of ten differing designs of tubing 400a, 400b, 400c, 400d, 400e, 400f, 400g, 400h, 400i, and 400j (or collectively tubing 400a-j) are each illustrated in uncompressed and fully compressed states. The tubing 400a-j differ from each other with respect to an individual tubing's rib height as a percentage of its inner radius. For example, tubing 400a has no ribs; the height of the ribs of the tubing 400b are each 6% of the inner radius of tubing 400b; the height of the ribs of the tubing 400c are each 13% of the inner radius of tubing 400c; the height of the ribs of the tubing 400d are each 21% of the inner radius of tubing 400d; the height of the ribs of the tubing 400e are each 32% of the inner radius of tubing 400e; the height of the ribs of the tubing 400f are each 43% of the inner radius of tubing 400f; the height of the ribs of the tubing 400g are each 52% of the inner radius of tubing 400g; the height of the ribs of the tubing 400h are each 60% of the inner radius of tubing 400h; the height of the ribs of the tubing 400i are each 70% of the inner radius of tubing 400i; and the height of the ribs of the tubing 400j are each 79% of the inner radius of tubing 400j.

In order to investigate and discover the optimal rib height for kink and compression tolerance, the inventors created a solid model of each design of the tubing 400a-j. Then, using finite element analysis (FEA), the fully compressed state for each design of the tubing 400a-j was simulated (as shown). From there, the fully compressed open area of each design of the tubing 400a-j was calculated.

Figure 10:
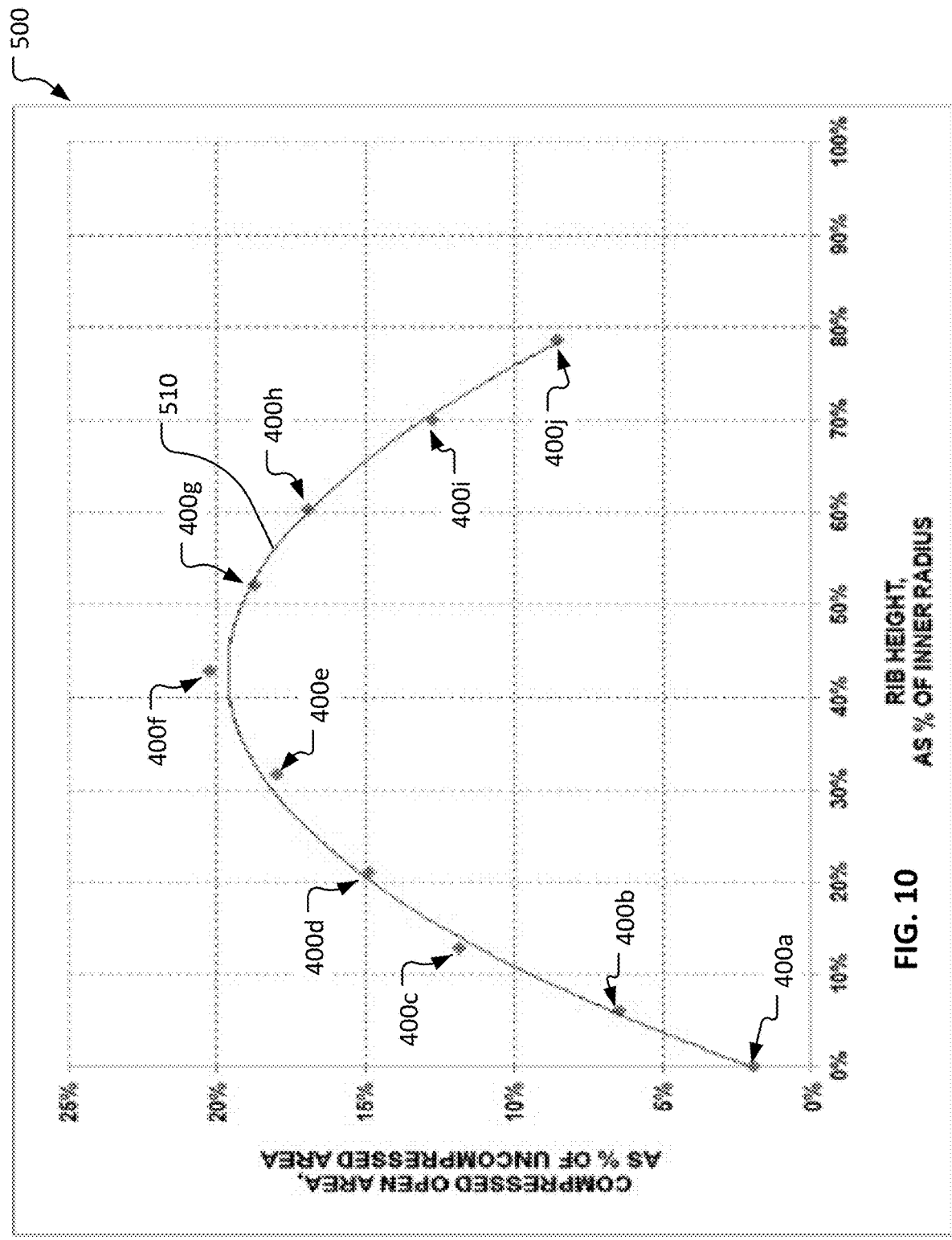
FIG. 10 is a graph that illustrates the compressed open area of tubes having various rib heights.

Referring also to FIG. 10, the results of the calculations of the fully compressed open areas of each design of the tubing 400a-j are shown in a graph 500. That is, the graph 500 is a plot of the fully compressed open area of each design of the tubing 400a-j as a function of each tubing's rib height as a percentage of its inner radius. The individual open area value for each design of the tubing 400a-j is shown, and a fit line 510 is also shown.

The graph 500 shows that the tubing 400f yields the greatest amount of open area when fully compressed. The ribs of the tubing 400f are each 43% of the inner radius of tubing 400f. The open area of the tubing 400f while it is in the fully compressed state is about 20% of the uncompressed open area of the tubing 400f. The fit line 510 shows that the open area while fully compressed is effectively optimal in a range of about 40% to about 46% in terms of rib height as a percentage of inner radius.

The inventors also experimented with the kink and compression tolerance effects of various numbers of ribs in the tubing. For example, the inventors experimented with zero ribs, two ribs, three ribs, four ribs, five ribs, six ribs, and seven ribs. The results of such experiments demonstrated that the three rib design was superior than the others.

Figure 11:
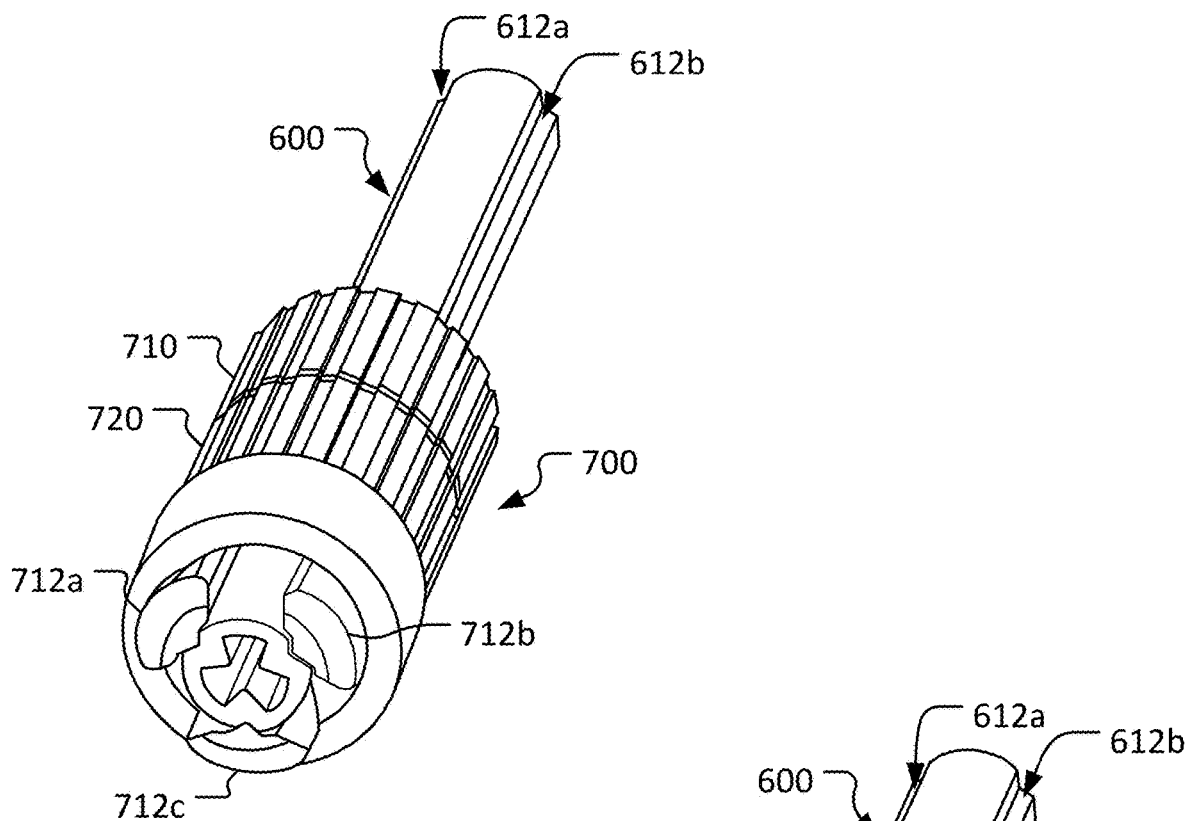
FIG. 11 shows a perspective view of another example tube that is kink and compression tolerant, and an example closure mechanism on the tube.
Figure 12:
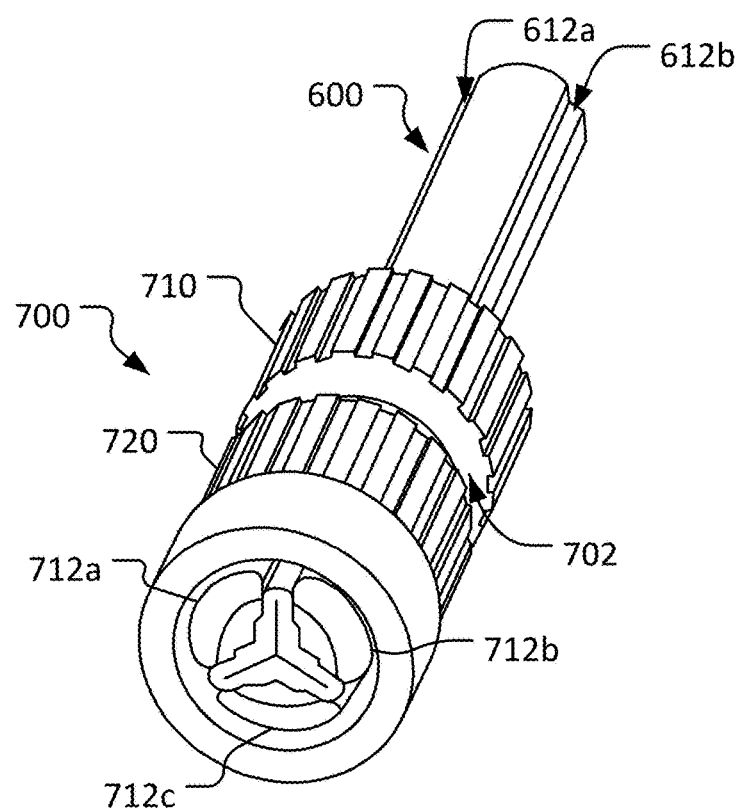
FIG. 12 shows a perspective view of the arrangement of FIG. 11 with the closure mechanism fully clamping the tube closed.

Referring to FIGS. 11 and 12, while the tubing described herein includes internal ribs that advantageously provide kink and compression tolerance (e.g., the tubing will continue to have open luminal area even when fully compressed in the manner described above), in some cases it is desirable or necessary to fully close the lumen of such tubing. Accordingly, a collet-like tube closure device 700 can be used to fully close internally ribbed tubing 600 (tubing 600 is internally the same as the tubing 300 and tubing 400f described above). In FIG. 11, the internally ribbed tubing 600 is illustrated as fully open, and in FIG. 12 the internally ribbed tubing 600 is illustrated as fully closed because the tube closure device 700 is acting on the tubing 600.

Figure 13:
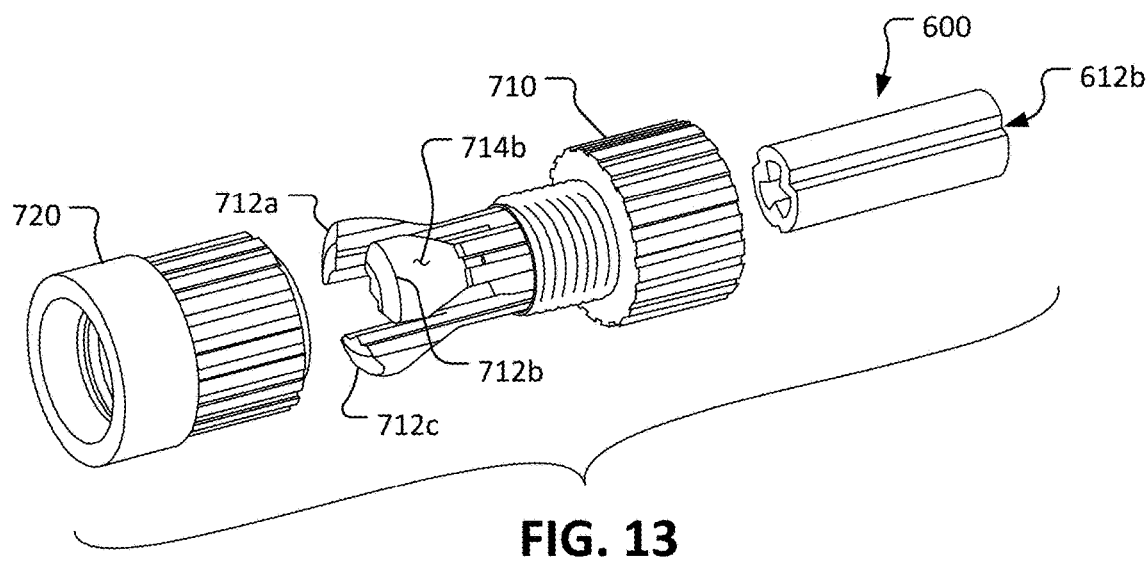
FIG. 13 shows an exploded perspective view of the closure mechanism of FIG. 11.
Figure 14:
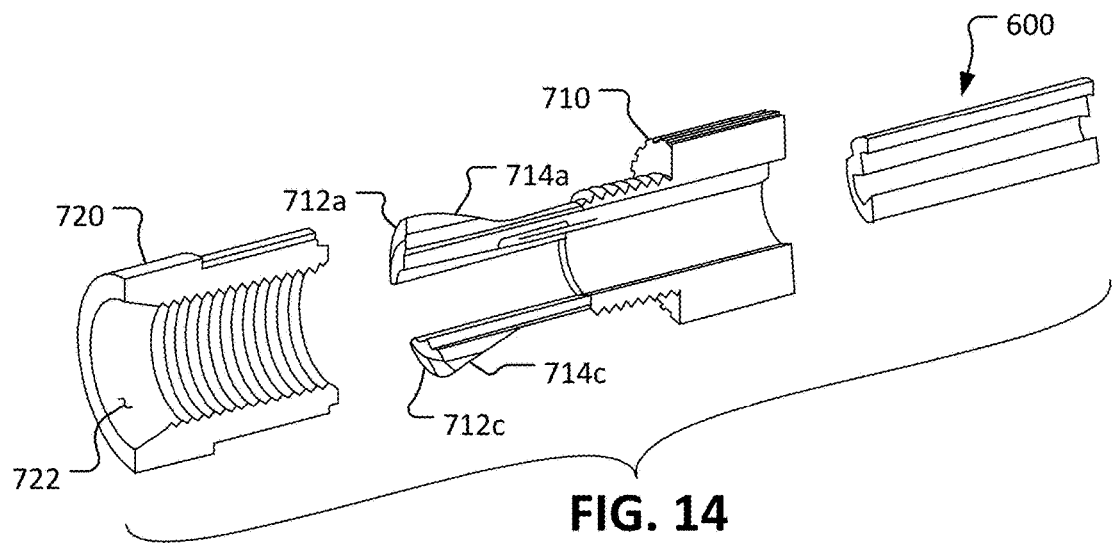
FIG. 14 shows an exploded longitudinal cross-sectional perspective view of the closure mechanism of FIG. 11.

Referring also to FIGS. 13 and 14, the collet-like tube closure device 700 includes an externally threaded sleeve 710 and an internally threaded clamp collar 720. The externally threaded sleeve 710 and the internally threaded clamp collar 720 are threadedly coupled together. Accordingly, when the internally threaded clamp collar 720 is rotated in relation to the externally threaded sleeve 710 the internally threaded clamp collar 720 will move longitudinally in relation to the externally threaded sleeve 710. For example, while in FIG. 11 the externally threaded sleeve 710 and the internally threaded clamp collar 720 are essentially abutting against each other, in FIG. 12 there is a gap 702 between the externally threaded sleeve 710 and the internally threaded clamp collar 720.

The externally threaded sleeve 710 defines an opening that slidingly receives the tubing 600. Three jaws 712a, 712b, and 712c are connected to and extend longitudinally from the externally threaded sleeve 710 like cantilevered beams. The jaws 712a, 712b, and 712c are radially deflectable in relation to the externally threaded sleeve 710.

Each of the three jaws 712a, 712b, and 712c includes a respective ramp surface 714a, 714b, and 714c. The internally threaded clamp collar 720 includes a corresponding annular ramp surface 722 that slidingly mates against the ramp surfaces 714a, 714b, and 714c.

The internally threaded clamp collar 720 can be threadedly adjusted in relation to the externally threaded sleeve 710 such that the ramp surface 722 adjustably exerts pressure on each of the three jaws 712a, 712b, and 712c to force the jaws 712a, 712b, and 712c radially inward. For example, in FIG. 12 the three jaws 712a, 712b, and 712c are depicted as being forced radially inward by the internally threaded clamp collar 720, whereas in FIG. 11 the three jaws 712a, 712b, and 712c are depicted as radially positioned such that the tubing 600 is uncompressed (because the internally threaded clamp collar 720 is not pressing the three jaws 712a, 712b, and 712c radially inward).

In the depicted embodiment, the tubing 600 defines three longitudinally-extending grooves 612a, 612b, and 612c extending along the outer surface of the tubing 600. The three longitudinally-extending grooves 612a, 612b, and 612c are in radial alignment with the three internal ribs of the tubing 600 (see e.g., the example internal ribs 310a, 310b, and 310c of tubing 300 as shown in FIG. 4).

The three jaws 712a, 712b, and 712c are matingly positioned within the three longitudinally-extending grooves 612a, 612b, and 612c. That is, the jaw 712a is positioned within the groove 612a, the jaw 712b is positioned within the groove 612b, and the jaw 712c is positioned within the groove 612c. When the externally threaded sleeve 710 is slid longitudinally along the tubing 600, the three jaws 712a, 712b, and 712c slide within the three longitudinally-extending grooves 612a, 612b, and 612c.

Because the three longitudinally-extending grooves 612a, 612b, and 612c are in radial alignment with the three internal ribs of the tubing 600, and because the three jaws 712a, 712b, and 712c are positioned within the three longitudinally-extending grooves 612a, 612b, and 612c, it follows that the three jaws 712a, 712b, and 712c are in radially alignment with the three internal ribs of the tubing 600. Accordingly, when the three jaws 712a, 712b, and 712c are forced radially inward by the internally threaded clamp collar 720, the three internal ribs of the tubing 600 are forced toward the center of the tubing 600. The apices of the three internal ribs of the tubing 600 meet each other at the center of the tubing 600. As a result the tubing 600 becomes fully closed (there is no open portion of the lumen of the tubing 600).

Again, in the arrangement of FIG. 11 the internally threaded clamp collar 720 is positioned in relation to the three jaws 712a, 712b, and 712c such that the ramp surface 722 of the internally threaded clamp collar 720 is not exerting sufficient pressure on the ramp surfaces 714a, 714b, and 714c of the three jaws 712a, 712b, and 712c to cause the jaws 712a, 712b, and 712c to compress the tubing 600. Then, in order to begin to close the tubing 600, a user can twist the internally threaded clamp collar 720 in relation to the externally threaded sleeve 710. In doing so, the internally threaded clamp collar 720 will move longitudinally away from the externally threaded sleeve 710 and the ramp surface 722 of the internally threaded clamp collar 720 will begin to exert pressure on the ramp surfaces 714a, 714b, and 714c of the three jaws 712a, 712b, and 712c to cause the jaws 712a, 712b, and 712c to compress the tubing 600. If so desired, the user can continue twisting the internally threaded clamp collar 720 in relation to the externally threaded sleeve 710 until the ramp surface 722 of the internally threaded clamp collar 720 exerts sufficient pressure on the ramp surfaces 714a, 714b, and 714c of the three jaws 712a, 712b, and 712c to cause the jaws 712a, 712b, and 712c to fully close the tubing 600 by causing the three internal ribs of the tubing 600 meet each other at the center of the tubing 600 (as depicted in FIG. 12).

Figure 15:
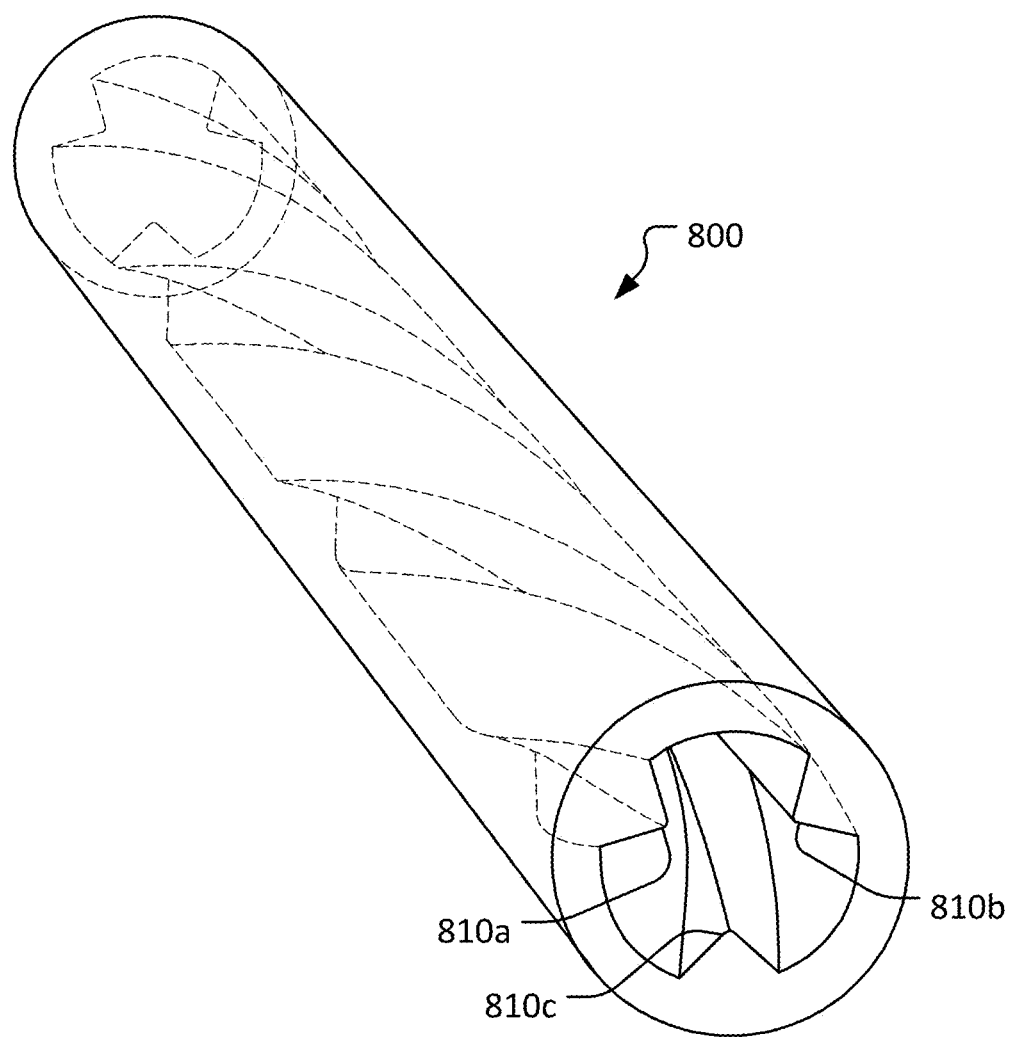
FIG. 15 is a perspective view of another example tube that is kink and compression tolerant.

A number of embodiments of the invention have been described. Nevertheless, it will be understood that various modifications may be made without departing from the spirit and scope of the invention. For example, FIG. 15 illustrates another example kink and compression tolerant medical tubing 800. As with the tubing 300 described above, the tubing 800 includes three ribs 810a, 810b, and 810c. In a manner that is analogous to the tubing 300, the ribs 810a-c can be triangular and can have, for example, a rib height that is 43% of the inner radius of the tubing 800. However, whereas the ribs 310a, 310b, and 310c of the tubing 300 extend parallel to the longitudinal axis of the tubing 300, the ribs 810a, 810b, and 810c spiral around the longitudinal axis of the tubing 800. In some embodiments, the ribs 810a, 810b, and 810c extend helically around the longitudinal axis of the tubing 800. The angle that the ribs 810a, 810b, and 810c extend in relation to the longitudinal axis of the tubing 800 can be in a range between 5 degrees to 15 degrees, or between 10 degrees to 20 degrees, or between 15 degrees to 25 degrees, or between 20 degrees to 30 degrees, or between 25 degrees to 35 degrees, or between 30 degrees to 40 degrees, or between 35 degrees to 45 degrees, or more than 45 degrees. This tubing design with spirally extending internal ribs 810a, 810b, and 810c can advantageously provide consistent bending/flexure properties regardless of the bend direction relative to the tubing 800.

While the tubing 300 has been described as being made from PVC, in some embodiments, the tubing 300 can be made from any other suitable polymeric material such as, but not limited to, polyethylene, polyurethanes, nylons, fluoropolymers, natural rubber, natural rubber latex, synthetic rubber, thermoplastic rubbers, silicone, and the like, and combinations thereof.

While the tubing 300 has been described as having an outer diameter of 6.0 mm, in some embodiments, the tubing 300 has an outer diameter in a range of 1.0 mm to 5.0 mm, or 3.0 mm to 7.0 mm, 5.0 mm to 9.0 mm, or 7.0 mm to 1.1 cm, or 9.0 mm to 1.3 cm, or 1.1 cm to 1.5 cm, or 1.3 cm to 1.7 cm, or 1.5 cm to 1.9 cm, or 1.7 cm to 2.1 cm, and/or more than 2.1 cm. While the tubing 300 have been described as having an inner diameter of 4.0 mm, in some embodiments, the tubing 300 has an inner diameter in a range of 1.0 mm to 5.0 mm, or 3.0 mm to 7.0 mm, 5.0 mm to 9.0 mm, or 7.0 mm to 1.1 cm, or 9.0 mm to 1.3 cm, or 1.1 cm to 1.5 cm, or 1.3 cm to 1.7 cm, or 1.5 cm to 1.9 cm, or 1.7 cm to 2.1 cm, and/or more than 2.1 cm.

While in the depicted embodiment of the tubing 300 there is no reinforcing wire/material within the wall of the tubing 300, in some embodiments, one or more wires or other types of reinforcing materials can be included within the wall of the tubing 300.

While the depicted embodiment of the tubing 300 includes three internal ribs 310a-c, in some embodiments, one, two, four, five, six, seven, or more than seven ribs are included.

While the depicted embodiment of the tubing 300 the rib height 330 is 43% of the radius 320 of the tubing 300, in some embodiments, the rib height 330 is in a range of 42% to 44%, or 40% to 46%, or 38% to 48%, or 36% to 50%, or 34% to 38%, or 36% to 40%, or 38% to 42%, or 40% to 44%, or 42% to 46%, or 44% to 48%, or 46% to 50%, or 48% to 52%, or 50% to 54% of the radius 320 of the tubing 300.

While the ribs 310a-c have been described as triangular shaped, in some embodiments, other shapes as used such as, but not limited to, rectangular, ovular, and so on. While in the depicted embodiment the ribs 310a-c are solid, in some embodiments, the ribs 310a-c are hollow (have open space within the boundaries of the ribs 310a-c).

Figure 16:
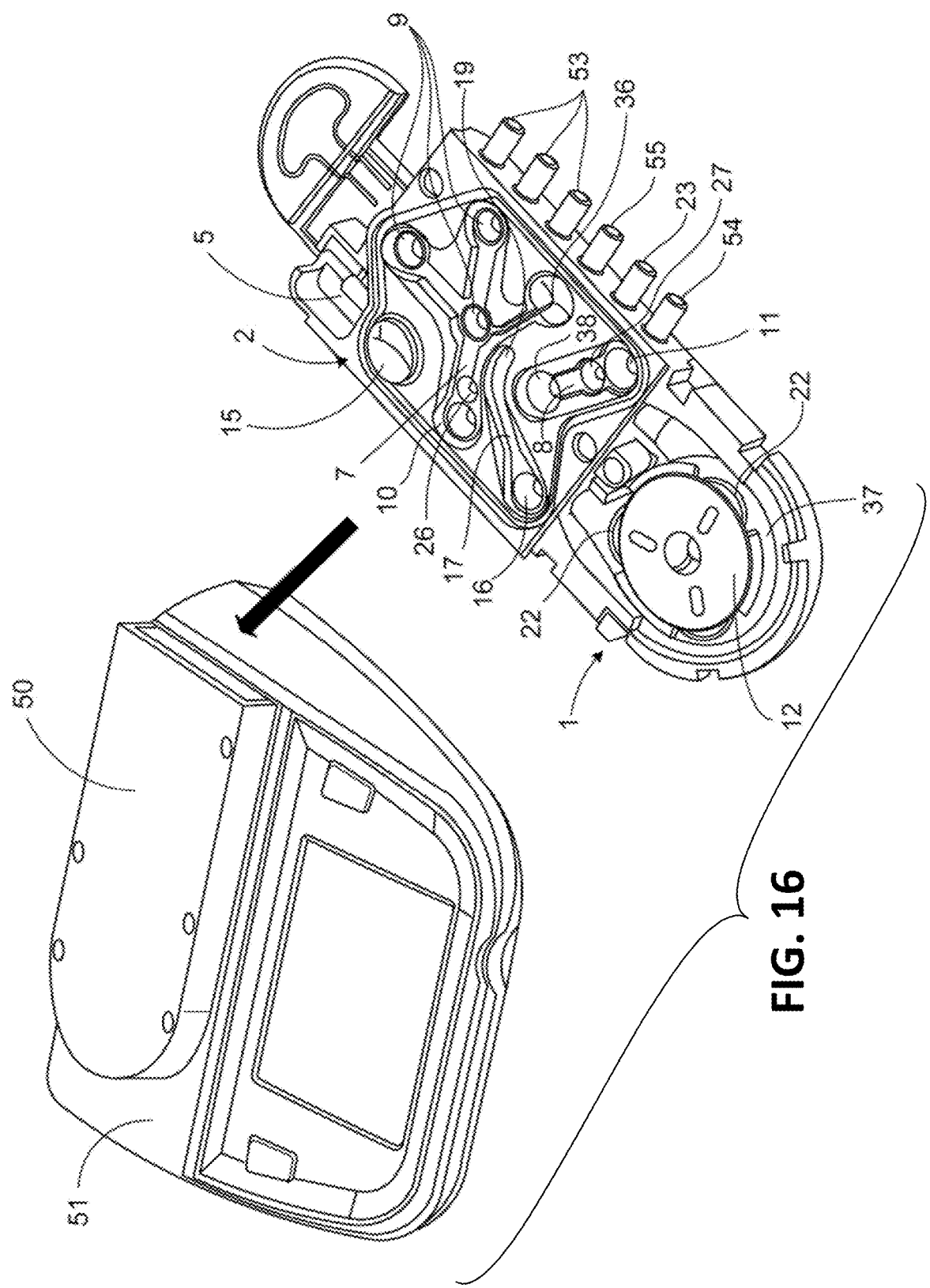
FIG. 16 is a perspective view of an alternative PD system that includes a PD cycler and a cartridge that, when connected to the PD cycler, forms a peristaltic pump.

While the PD system 100 has been described and illustrated as including piston pumps, in some embodiments, a PD system that is otherwise similar in construction and function to the PD system 100 may include one or more peristaltic pumps instead of piston pumps. FIG. 16, for example, illustrates a PD system 500 including a cycler 51 and a cartridge 2 (e.g., a liquid distribution system) that, when connected to the cycler 51, forms a peristaltic pump.

The cartridge 2 includes a pumping element 1, a first hub chamber 7, and a second hub chamber 8. The first chamber 7 includes a pump inlet 26 that can be connected to the pumping element 1 via a pump enter line, a liquid supply port 9 with a valve that can be connected to a liquid supply container via a liquid supply line, and a patient port 10 with a valve that can be connected to a patient via a patient line 5. In some embodiments, the patient line 5 can be kink and compression tolerant tubing (e.g., like the tubing 300 described above in reference to FIGS. 3-8, and/or like the tubing 600 described above in reference to FIGS. 11-14, and/or like the tubing 800 described above in reference to FIG. 15). The second hub chamber 8 includes a pump outlet 27 that can be connected to the pumping element 1 via a pump exit line, a drain port 11 with a valve that can be connected to a drain collector via a drain line along which a chemical testing device 200 positioned (e.g. as shown in FIG. 17), and a patient port 16 with a valve that can be connected to a patient 4 via the patient line 5.

The cartridge 2 further forms a cavity 15, which forms part of a pressure sensor. The first hub chamber 7 has three liquid supply ports 9, one patient port 10, one pump inlet 26, and a cavity 36 that forms part of a pressure sensor. The second hub chamber 8 has a patient port 18, a drain port 11, and a pump outlet 27. The cartridge 2 also includes a warmer chamber 17, which includes a warmer port 19 and a patient port 16. The warmer port 19 is connected to a warmer 28 (shown in FIG. 17) via a warmer tube connector 55 and a warmer exit line 30. The patient port 16 is connected to the patient line 5. The second hub chamber 8 includes a warmer port 38 connected to a warmer 28 via a warmer tube connector 23 and a warmer enter line 29.

The pumping element 1 includes a pump casing 45, which contains three rollers 22 maintained around a center of the pump casing 45 by a roller separator 12. The space between the roller separator 12 and the pump casing 45 defines a pump race 21 in which a flexible tube 37 is disposed. The flexible tube 37 is connected to the pump enter line 56 and the pump exit 57 line. The rollers 22 may be motor driven by a shaft 52 (shown in FIG. 18) in such a way as to progressively compress the flexible tube 37, thereby resulting in a peristaltic movement of fluid contained within and along the flexible tube 37. Accordingly, the pump casing 45, the rollers 22, the roller separator 12, and the pump race 21 together form a peristaltic pump by which liquid (e.g., dialysate) can be moved through the PD system 500.

Figure 17:
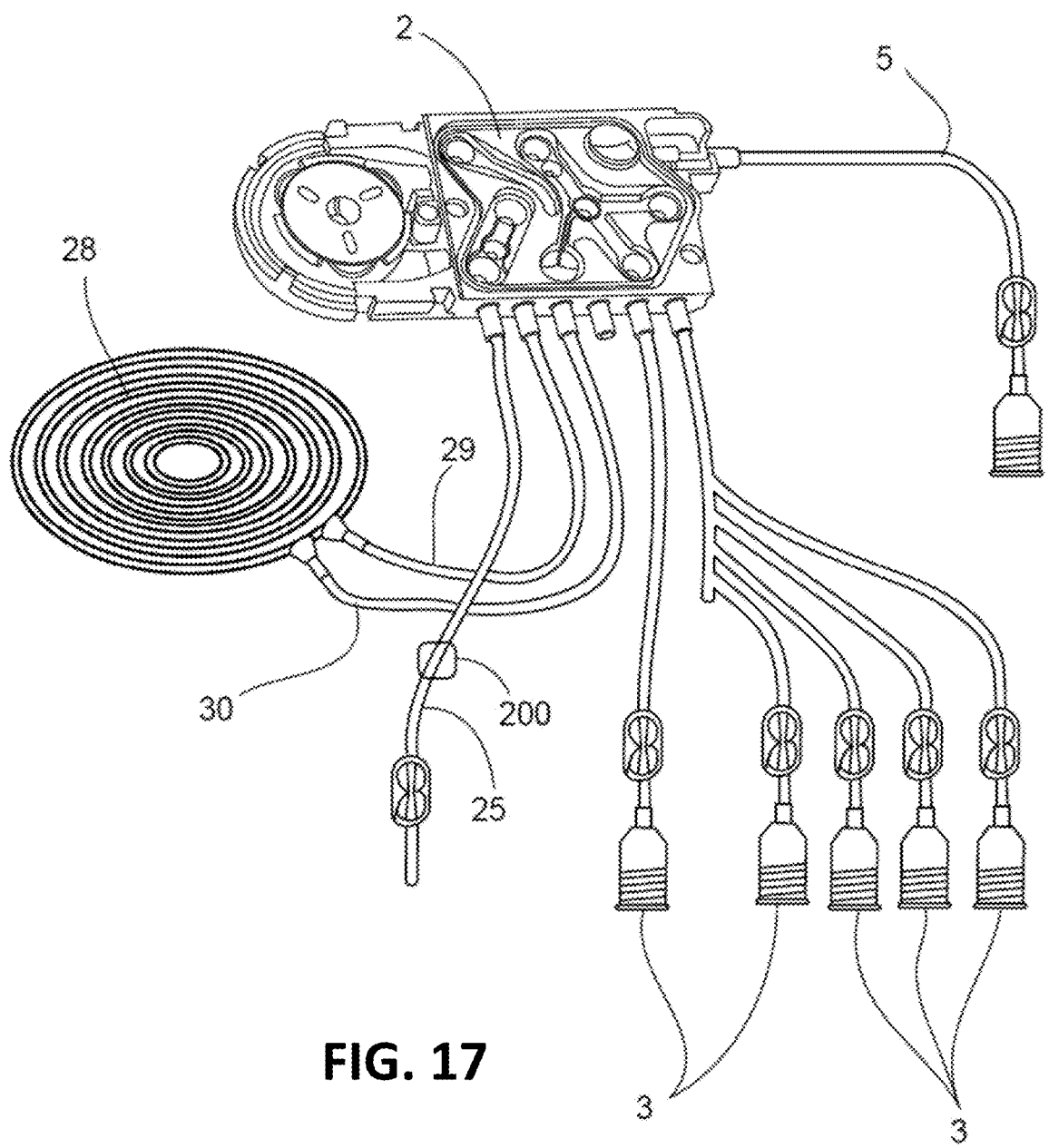
FIG. 17 is a perspective view of the cartridge of the PD system of FIG. 16, assembled with various fluid lines of the PD system of FIG. 16.

FIG. 17 shows an assembly including the cartridge 2, a patient line 5, supply bags 3, a warmer enter line 29, a warmer outer line 30, a warmer pouch 28 to be put into contact with a warming plate, a drain line 25, and the chemical testing device 25 installed to the drain line 25. In some embodiments, the patient line 5 can be kink and compression tolerant tubing (such as the tubing 300 described above in reference to FIGS. 3-8, the tubing 600 described above in reference to FIGS. 11-14, or the tubing 800 described above in reference to FIG. 15).

Figure 18:
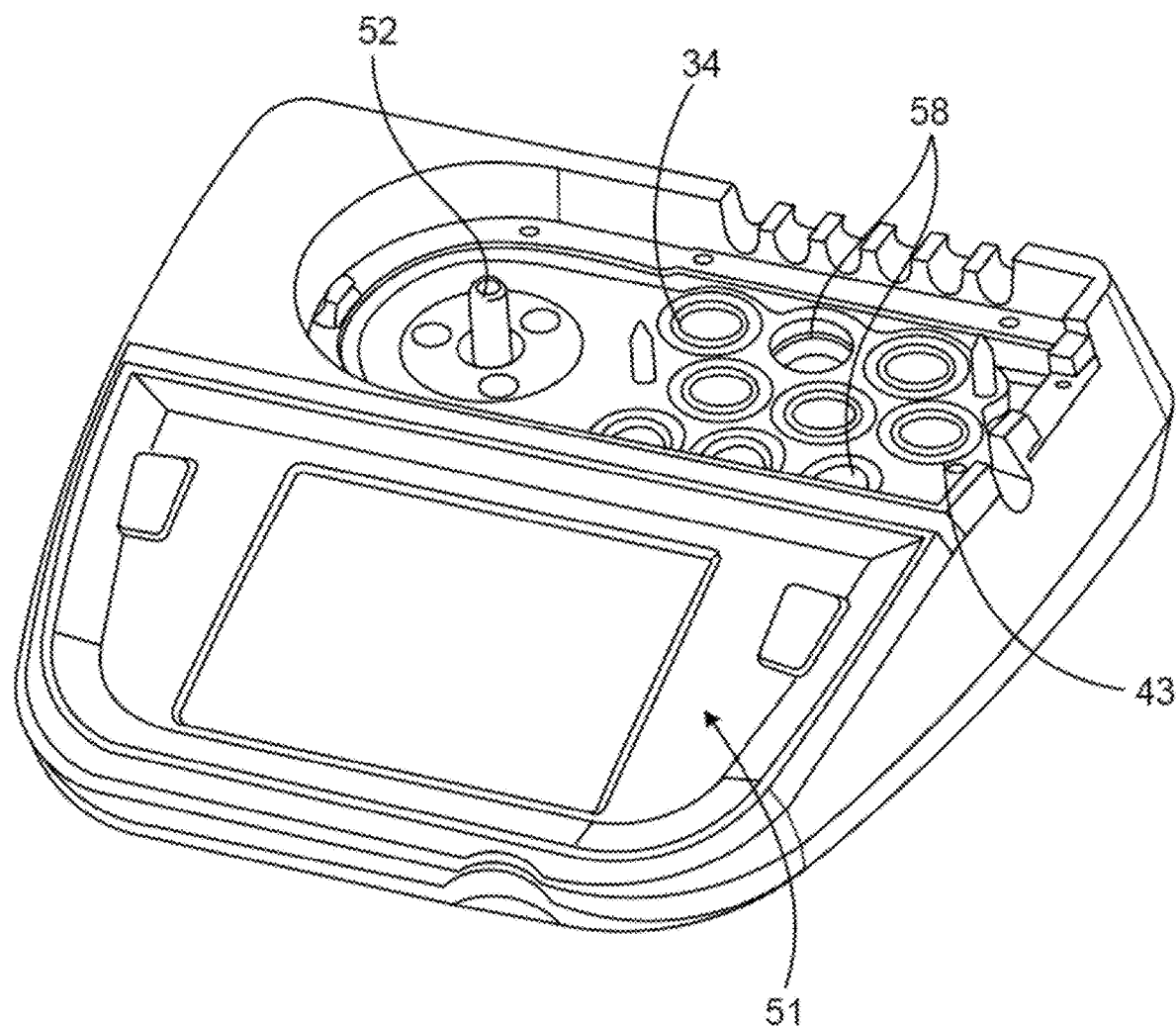
FIG. 18 is a perspective view of the PD cycler of the PD system of FIG. 16, with a cartridge slot of the PD cycler omitted.
Figure 19:
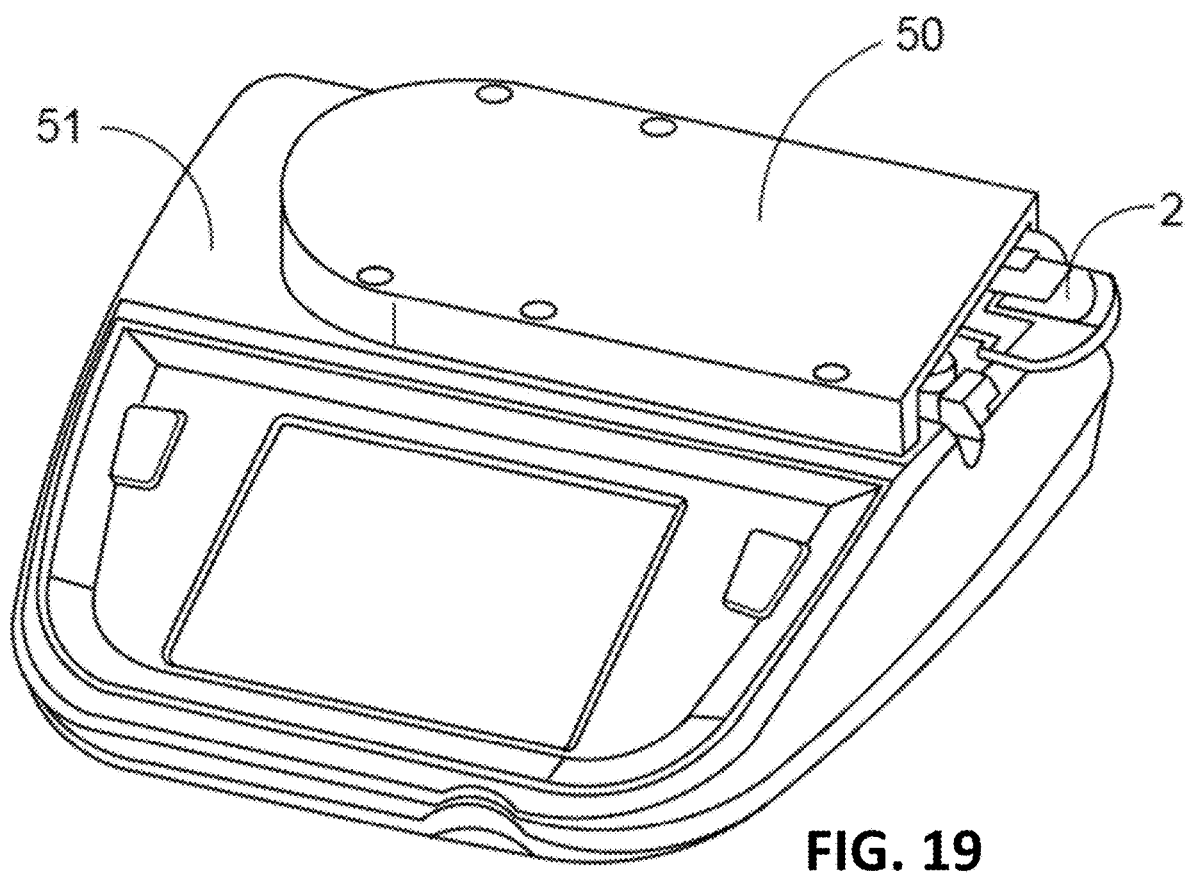
FIG. 19 is a perspective view of the PD cycler of FIG. 16 in an open configuration with the cartridge disposed therein.
Figure 20:
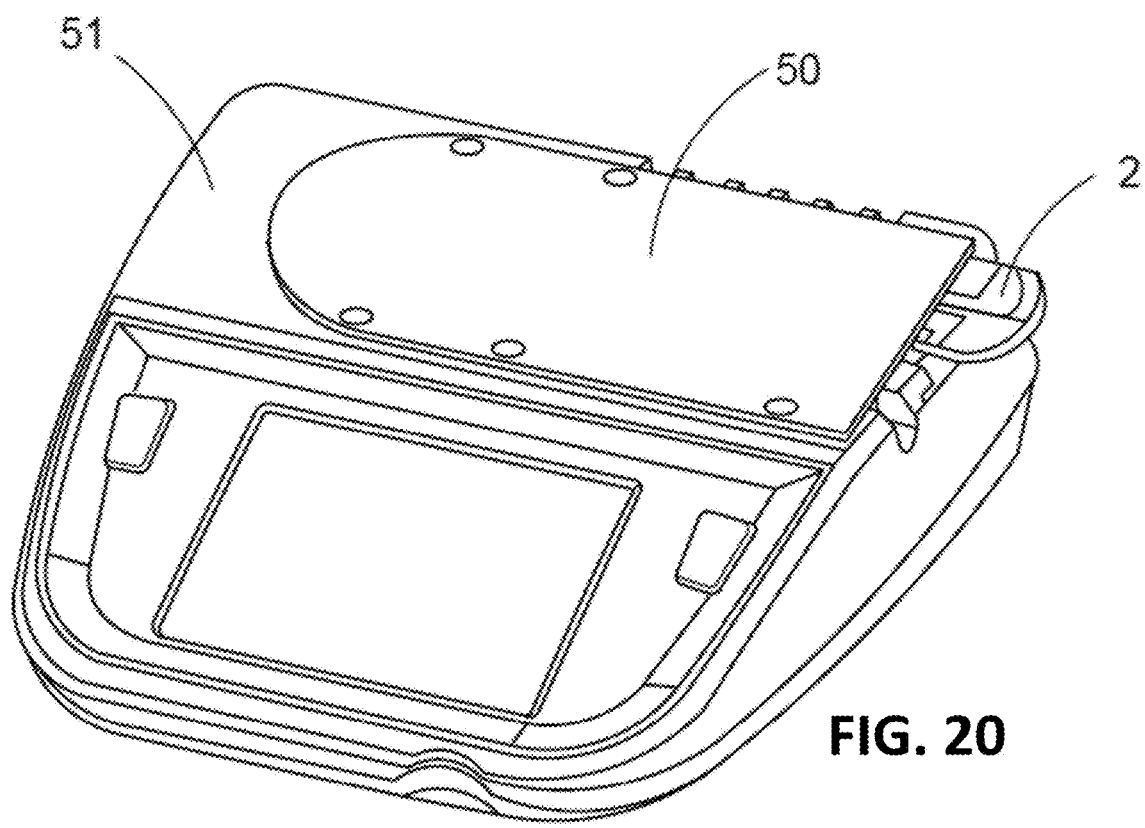
FIG. 20 is a perspective view of the PD cycler of FIG. 16 in a closed configuration with the cartridge disposed therein.

FIG. 18 shows the cycler 51 with the slot 50 and the cartridge 2 omitted to illustrate various internal features of the cycler 51. The cycler 51 includes a driving zone, which includes a several actuators 34 and a motor shaft 52 for interfacing with the rollers 22. The cycler 51 also includes an air sensor 43 situated close to the patient line 5 when the cartridge 2 is inserted. FIG. 19 shows the cycler 51 with the insertion slot 50 in an open configuration and with the cartridge 2 disposed within the insertion slot 50, while FIG. 20 shows the cycler 51 with the insertion slot 50 in a closed configuration and with the cartridge 2 disposed within the insertion slot 50.

Other embodiments are within the scope of the following claims.

What is claimed is:

1. A medical tubing system, comprising:
    a medical tube defining a central longitudinal axis and including internal ribs extending inwardly from an inner wall of the tube toward the central longitudinal axis, an outer wall of the tube defining grooves in radial alignment with the internal ribs and extending longitudinally along the tube; and
    a tube closure device comprising:
        a sleeve defining an opening that slidingly receives the tube, the sleeve including an externally threaded portion;

a set of jaws comprising three jaws that are each connected to and extending longitudinally from the externally threaded portion of the sleeve, each of the jaws including a ramp surface extending along an acute angle relative to the central longitudinal axis, and each of the jaws being radially deflectable in relation to the externally threaded portion of the sleeve; and a clamp collar positioned around at least portions of set of jaws, the clamp collar including an internally threaded portion that is threadedly coupled with the externally threaded portion of the sleeve, the clamp collar including an annular ramp surface that corresponds to and slidingly mates against the ramp surface of each of the jaws, the annular ramp surface extending from the internally threaded portion and defining an end opening of the clamp collar that is larger in diameter than the internally threaded portion.

2. The system of claim 1, wherein the clamp collar is longitudinally movable in relation to the set of jaws between: (i) a first position in which the set of jaws are in an open configuration and (ii) a second position in which the clamp collar deflects the set of jaws radially inward in comparison to the open configuration.

3. The system of claim 1, wherein while the tube closure device is positioned on the tube, each one of the internal ribs is radially alignable with a respective jaw of the set of jaws.

4. The system of claim 3, wherein the tube includes three internal ribs.

5. The system of claim 1, wherein each of the jaws is matingly positioned within a respective one of the grooves in the outer wall of the tube.

6. The system of claim 1, wherein each of the internal ribs includes an apex, and wherein the clamp collar can deflect the set of jaws radially inward such that the apices of the internal ribs meet each other at a center of the tube.

7. The system of claim 6, wherein the tube is fully closed when the apices of the internal ribs meet each other at the center of the tube.

* * * * *